US007066891B2

(12) United States Patent
Stadler et al.

(10) Patent No.: US 7,066,891 B2
(45) Date of Patent: Jun. 27, 2006

(54) METHOD AND APPARATUS FOR GAUGING SEVERITY OF MYOCARDIAL ISCHEMIC EPISODES

(75) Inventors: Robert W. Stadler, Shoreview, MN (US); Steven N. Lu, Fridley, MN (US); Gary W. King, Fridley, MN (US); Thomas R. Moore, Saline, MI (US)

(73) Assignee: Medtronic, Inc., Minneapolis, MN (US)

( * ) Notice: Subject to any disclaimer, the term of this patent is extended or adjusted under 35 U.S.C. 154(b) by 544 days.

(21) Appl. No.: 10/325,076

(22) Filed: Dec. 20, 2002

(65) Prior Publication Data

US 2004/0122478 A1 Jun. 24, 2004

(51) Int. Cl.
*A61B 5/02* (2006.01)
(52) U.S. Cl. .......................................... 600/508; 607/17
(58) Field of Classification Search ................ 600/508; 607/17
See application file for complete search history.

(56) References Cited

U.S. PATENT DOCUMENTS

| 5,199,428 | A | * | 4/1993 | Obel et al. ..................... 607/44 |
| 5,893,840 | A | | 4/1999 | Hull et al. |
| 6,049,730 | A | * | 4/2000 | Kristbjarnarson ........... 600/509 |
| 6,080,190 | A | | 6/2000 | Schwartz |
| 6,128,526 | A | | 10/2000 | Stadler et al. |
| 6,256,538 | B1 | * | 7/2001 | Ekwall ........................ 607/17 |
| 6,272,379 | B1 | * | 8/2001 | Fischell et al. ................. 607/5 |
| 6,324,421 | B1 | | 11/2001 | Stadler et al. |
| 6,339,720 | B1 | * | 1/2002 | Anzellini et al. ........... 600/517 |
| 6,368,284 | B1 | * | 4/2002 | Bardy ........................ 600/508 |
| 6,381,493 | B1 | | 4/2002 | Stadler et al. |
| 6,397,100 | B1 | | 5/2002 | Stadler et al. |
| 6,501,983 | B1 | * | 12/2002 | Natarajan et al. ........... 600/517 |
| 6,609,023 | B1 | * | 8/2003 | Fischell et al. ............. 600/515 |
| 2003/0045805 | A1 | * | 3/2003 | Sheldon et al. ............. 600/513 |

FOREIGN PATENT DOCUMENTS

EP         0 941 695 A2    9/1999

* cited by examiner

*Primary Examiner*—George Manuel
*Assistant Examiner*—Nichole R. Kramer
(74) *Attorney, Agent, or Firm*—Paul H. McDowall; Girma Wolde-Michael

(57) ABSTRACT

An implantable medical device (IMD) for gauging the severity of ischemia in a patient's heart includes a data collection module configured to receive data about the patient's heart, a data processing module configured to process the data to identify an episode of ischemia in the patient and to determine if the episode is stable or unstable, and a reporting module configured to provide an alarm to the patient if the episode is unstable. A method executable by an implantable medical device to detect ischemia in a human heart suitably includes the steps of receiving data about the heart at the implantable medical device, processing the data within the implantable medical device to determine the severity of ischemia, and providing a response from the implantable medical device to the patient if ischemia is indicated.

17 Claims, 4 Drawing Sheets

METHOD AND APPARATUS FOR GAUGING
SEVERITY OF MYOCARDIAL ISCHEMIC
EPISODES

FIELD

The invention relates to cardiac health and, more particularly, to devices and techniques for gauging the severity of myocardial ischemia.

BACKGROUND

Ischemia is a medical condition caused by an insufficient supply of blood to an organ, usually due to a blocked artery. Myocardial ischemia, for example, is an intermediate condition in coronary artery disease during which heart tissue fails to receive oxygen and other nutrients from the blood. Ischemia remains one of the most prevalent causes of morbidity and mortality in the developed world.

Ischemic episodes can be symptomatic or silent (i.e. without observable symptoms), and the presence or absence of symptoms appears to be independent of the severity of the ischemia. According to the American Heart Association, millions of Americans may have silent ischemia. If even minor forms of ischemia remain untreated, affected heart tissue can eventually die, placing the patient at a high risk of having a heart attack with little or no warning.

Myocardial ischemia is traditionally classified as "stable" or "unstable", depending upon severity. Stable ischemia, the least alarming form of ischemia, is caused by a high demand for oxygen by the myocardium during exertion and is relieved by rest. Although stable ischemia is of medical concern, many unaware patients live with stable ischemia for months or years without serious medical repercussions. Unstable ischemia, which occurs when the patient is at rest or is not relieved by rest, is caused by a sudden decrease in blood supply to the heart and is generally considered to be a medical emergency. This type of ischemia is frequently caused by atherosclerotic plaque rupture and clot formation inside the arteries. While unstable ischemia occasionally resolves spontaneously with no long-term sequelae, the condition frequently persists until myocardial infarction occurs.

Physicians consider various factors in further classifying the severity of stable and unstable episodes of ischemia. Even stable ischemia can be of great concern if it affects a relatively large section of the myocardium, for example, or if the episode persists for a relatively long period of time (e.g. on the order of thirty minutes or so), since such episodes can lead to myocardial cell stunning or death. Further, physicians often compare episodes of ischemia to prior episodes experienced by the patient to identify a typical episodes.

Although many techniques of diagnosing ischemia have existed for some time, these techniques have typically required the patient to consult a health care provider to be effective. Electrocardiograms (ECG) or electrograms (EGM), for example, have been shown to be effective in diagnosing ischemia by identifying abnormalities in the patient's cardiac activity. Variations in the ST segment of the patient's "PQRST" ECG waveform, for example, have been shown to indicate episodes of myocardial ischemia. U.S. Pat. No. 6,128,526 to Stadler et al. describes one type of ischemia detector that observes variation in the ST segment to identify an ischemic condition. Other ischemia detection techniques have relied upon measures of heart activity, patient workload and other factors.

Early detection of myocardial ischemia provides the opportunity for a wide range of effective therapies such as revascularization, neural stimulation, and drug delivery to reduce cardiac workload or to improve cardiac circulation. Because many episodes of myocardial ischemia occur without causing excessive pain or other noticeable warning signs, however, ischemia frequently goes undetected. Gauging the severity of ischemia has historically required that the patient be physically present at a health care facility to obtain diagnosis from an ECG, EGM or the like. As a result, ischemia frequently remains untreated until a major episode occurs and the patient arrives at an emergency room or trauma center. Accordingly, it is desirable to create a technique for identifying ischemia at an early stage, while the condition remains highly treatable and before a major episode occurs. In addition, it is desirable to create a device and/or technique that is capable of gauging the severity of ischemia so that the condition can, be appropriately treated. Furthermore, other desirable features and characteristics of the present invention will become apparent from the subsequent detailed description and the appended claims, taken in conjunction with the accompanying drawings and this background of the invention.

BRIEF DESCRIPTION OF THE EXEMPLARY EMBODIMENTS

According to various aspects of the invention, an implantable medical device for gauging the severity of ischemia in a patient's heart includes a data collection module configured to receive data about the patient's heart, a data processing module configured to process the data to identify an episode of ischemia in the patient and to determine if the episode is stable or unstable, and a reporting module configured to provide an alarm to the patient if the episode is unstable. In another aspect, a method executable by an implantable medical device to detect ischemia in a human heart suitably includes the steps of receiving data about the heart at the implantable medical device, processing the data within the implantable medical device to determine the severity of ischemia, and providing a response from the implantable medical device to the patient if ischemia is indicated. The response provided may be dependent upon the severity of the ischemic episode, and may range from a simple warning to administration of therapy.

BRIEF DESCRIPTION OF DRAWINGS

Various exemplary embodiments will hereinafter be described in conjunction with the following drawing figures, wherein like numerals denote like elements, and.

DETAILED DESCRIPTION OF EXEMPLARY EMBODIMENTS

The following detailed description is exemplary and not intended to limit the invention or the application and uses of the invention. Furthermore, there is no intention to be limited by any theory presented in the preceding background of the invention or the following detailed description of the drawings.

According to various embodiments, an implantable medical device (IMD) continuously gathers and monitors data regarding a patient's cardiac state to quickly identify episodes of myocardial ischemia. One technique for identifying ischemia involves monitoring the ST segment of the patient's PQRST waveform to identify elevation or depression. Other factors such as changes in cardiac conduction time may additionally or alternatively be monitored. When an ischemic episode is identified, the IMD gauges the severity of the episode by determining, for example, whether the episode is occurring while the patient is active or at rest. Depending upon the severity of the episode, an appropriate response is triggered. In various embodiments, the IMD stores diagnostic data in a memory when the episode is determined to be of relatively low severity and activates an alarm to the patient if the episode requires immediate medical attention. In further embodiments, the IMD administers an appropriate therapy or other response when such treatment is warranted. As used herein, the term "response" is intended to broadly encompass any type of medical response, alarm, report or the like, as well as any of the various therapies that may be provided by the IMD to the patient.

Figure 1:
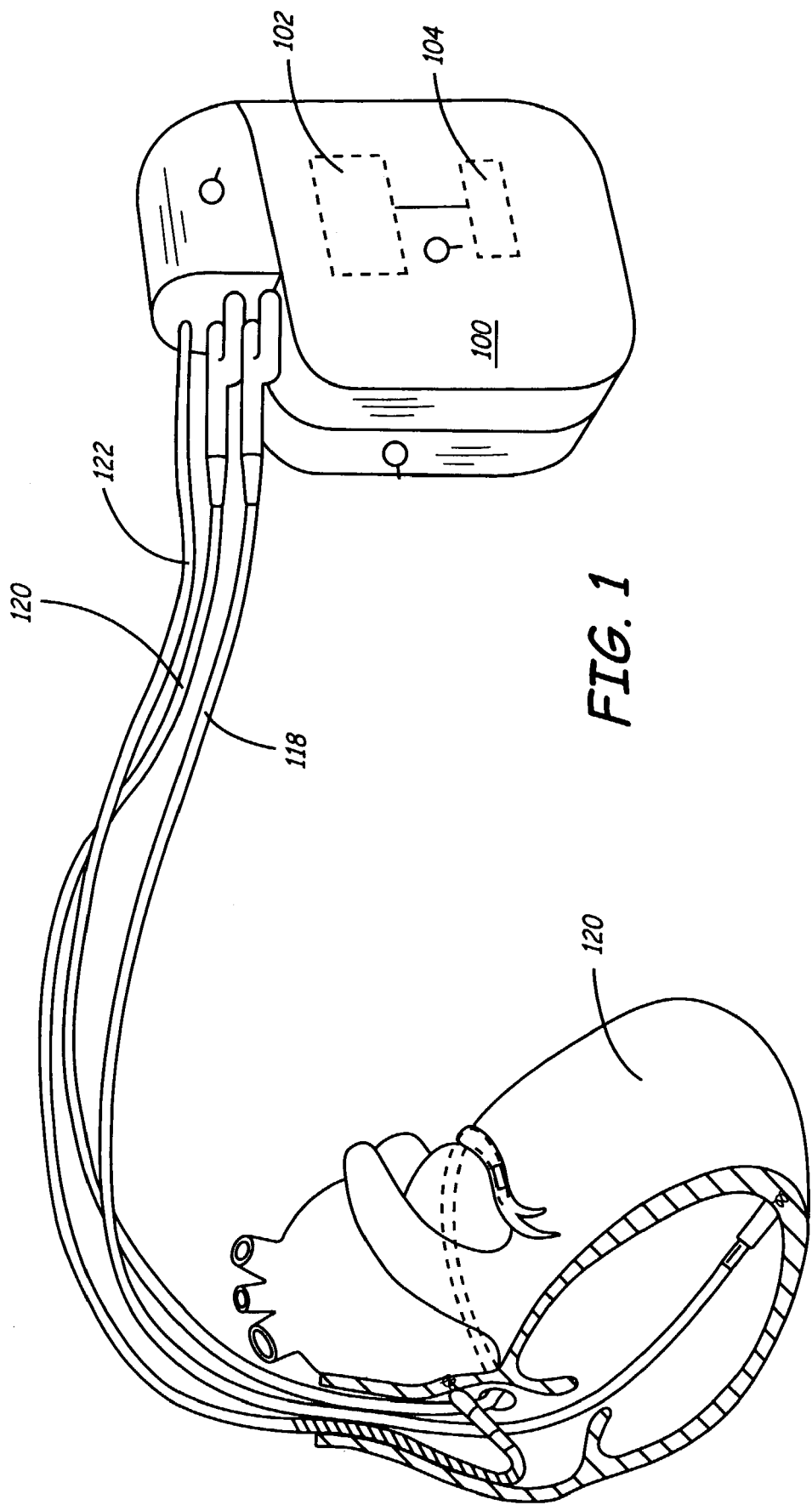
FIG. 1 is a diagram illustrating an exemplary implantable medical device in association with a heart.

With reference now to FIG. 1, an exemplary implantable medical device (IMD) 100 is connected to monitor a patient's heart 120. IMD 100 may be further configured to integrate both monitoring and therapy features, as will be described below. IMD 100 suitably collects and processes data about heart 120 from one or more sources to identify episodes of myocardial ischemia. In a further embodiment, IMD 100 may be configured to determine the degree of severity of the ischemic condition and to provide information that may be useful in selection of particular therapies. IMD 100 may quantify a change in cardiac conduction time, ST segment deviation or another parameter to estimate the extent of ischemia as a function of the observed quantity. IMD 100 may then select a particular therapy or response according to the estimated degree of severity of the ischemic episode.

As shown in FIG. 1, IMD 100 may be generally flat and thin to permit subcutaneous implantation within a human body, e.g., within upper thoracic regions or the lower abdominal region. IMD 100 may include a hermetically sealed housing that encloses a processor 102, a digital memory 104, and other components as appropriate to effect the desired functionality of the device.

Processor 102 may be implemented with any type of microprocessor, digital signal processor, application specific integrated circuit (ASIC), field programmable gate array (FPGA) or other integrated or discrete logic circuitry programmed or otherwise configured to provide functionality as described herein. Processor 52 executes instructions stored in digital memory 104 to provide functionality as described below. Instructions provided to processor 102 may be executed in any manner, using any data structures, architecture, programming language and/or other techniques. Digital memory 104 is any storage medium capable of maintaining digital data and instructions provided to processor 102 such as a static or dynamic random access memory (RAM), or any other electronic, magnetic, optical or other storage medium.

As further shown in FIG. 1, IMD 100 suitably receives one or more cardiac leads for connection to circuitry enclosed within the housing. In the example of FIG. 1, IMD 100 receives a right ventricular endocardial lead 118, a left ventricular epicardial lead 122, and a right atrial endocardial lead 120, although the particular cardiac leads used will vary widely from embodiment to embodiment. In addition, the housing of IMD 100 may function as an electrode, along with other electrodes that may be provided at various locations on the housing of IMD 10. In alternate embodiments, other data inputs, leads, electrodes and the like may be provided. Ventricular leads 118 and 122 may include, for example, pacing electrodes and defibrillation coil electrodes (not shown) in the event IMD 100 is configured to provide pacing, cardioversion and defibrillation. In addition, ventricular leads 118 and 122 may deliver pacing stimuli in a coordinated fashion to provide biventricular pacing, cardiac resynchronization or other benefits. IMD 100 may also obtain input data from other internal or external sources (not shown) such as a blood pressure monitor, pH monitor, accelerometer or the like.

In operation, IMD 100 suitably obtains data about heart 120 via leads 118, 120, 122, and/or other sources. This data is provided to processor 102, which suitably analyzes the data to identify episodes of ischemia, as described more fully below. Upon identification of an episode, IMD 100 suitably stores data about the episode in memory 104, and provides a response or report as appropriate. An identified ischemic episode can be treated by intervention of a physician or in an automated manner. In various embodiments, IMD 100 activates an alarm upon detection of the ischemic condition. Alternatively or in addition to alarm activation, IMD 100 selects a therapy and coordinates the delivery of the therapy by IMD 100 or another appropriate device. Optional therapies that may be applied in various embodiments may include drug delivery, electrical stimulation, neurostimulation, modifications in pacing rate, and/or the like. In addition, in the event the therapy involves electrical stimulation, the amplitude, frequency, or pulse width of stimulating current can be controlled according to the indicated degree of ischemia to achieve an optimum therapeutic effect. In a further embodiment, determination of the severity of ischemic tissue can be used to choose other types of therapy such as drug delivery, as well as types, dosages and durations of drug delivery.

Figure 2:
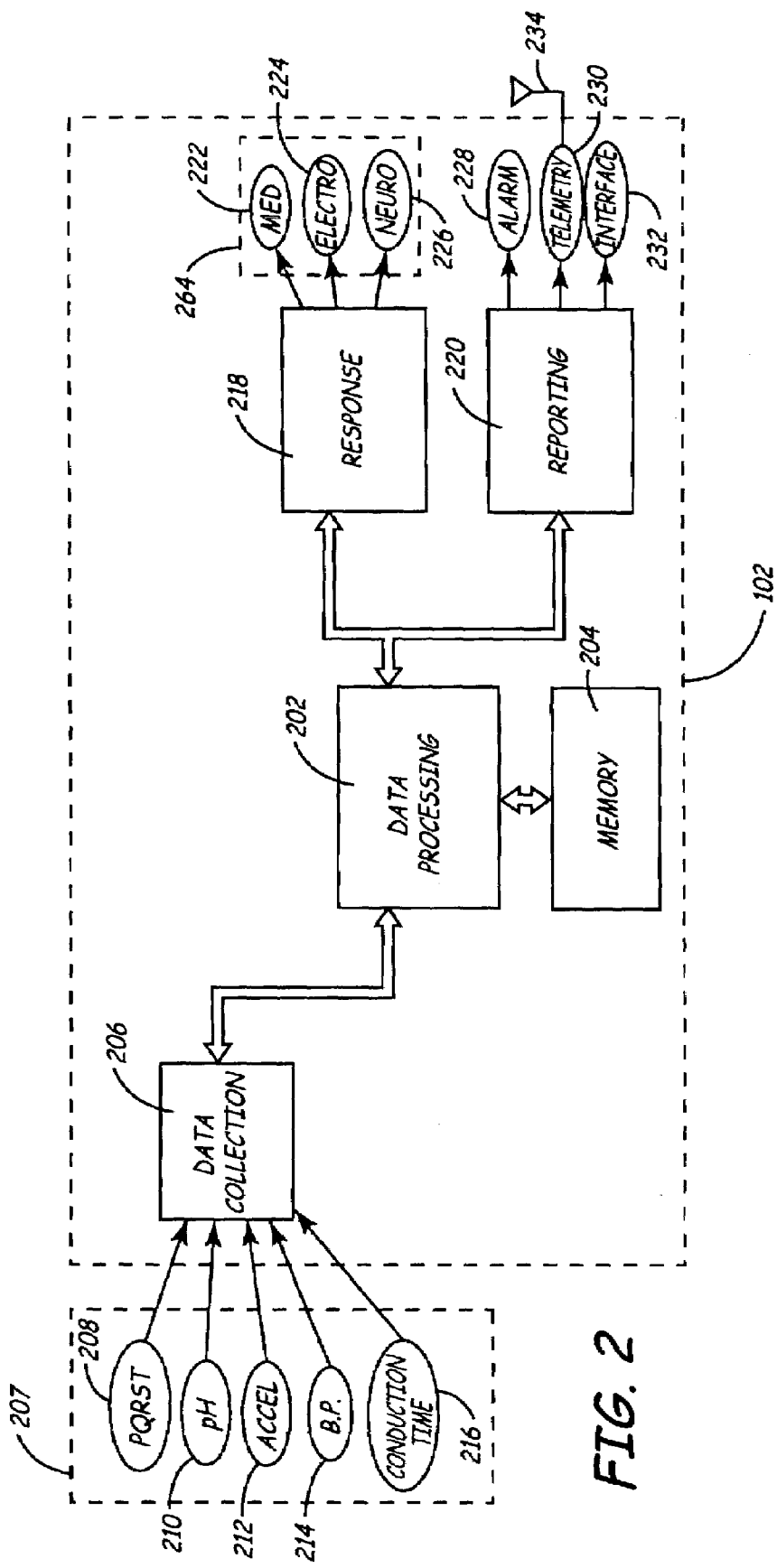
FIG. 2 is a conceptual block diagram of showing exemplary processing modules for an implantable medical device.

With reference now to FIG. 2, an exemplary data processing layout for an IMD 100 suitably includes a data collection module 206, a data processing module 202, a response module 218, and a reporting module 220. Each of the various modules may be implemented with computer-executable instructions stored in memory 104 and executing on processor 102 (FIG. 1), or in any other manner. The exemplary modules and blocks shown in FIG. 2 are intended to illustrate one logical model for implementing an IMD 100, and should not be construed as limiting. Indeed, the various practical embodiments may have widely varying software modules, data structures, applications, processes and the like. As such, the various functions of each module may in practice be combined, augmented, optimized or otherwise differently-organized in any fashion.

Data collection module 206 suitably interacts with one or more data sources 207 to obtain data about the patient. Data sources 207 include any source of information about the patient's heart, blood, temperature or the like. In various embodiments, data sources 207 include an ECG source 208 that provides electrical impulses or other observed signals that can be used to model the patient's electrocardiogram ("PQRST") waveform. Other data sources 207 may include a blood pH sensor 210, a blood pressure monitor 214, an accelerometer 212, a sensor 216 for determining cardiac conduction time and/or the like. Accelerometer 212 may include any type of motion sensor and/or a lead-based cardiac accelerometer that measures the strength of the cardiac contraction. The various data sources 207 may be provided alone or in any combination with each other, and may vary widely from embodiment to embodiment. Sensors for cardiac conduction time 216 and heart waveform 208 data could be combined into a single pair of electrodes, for example. Moreover, other data sources 207 such as temperature sensors or the like could additionally or alternatively be provided.

Data collection module 206 suitably receives data from each of the data sources 207 by polling each of the sources 207, by responding to interrupts or other signals generated by the sources 207, by receiving data at regular time intervals, or according to any other temporal scheme. Data may be received at data collection module 206 in digital or analog format according to any protocol. If any of the data sources generate analog data, data collection module 206 suitably translates the analog signals to digital equivalents using any form of analog-to-digital conversion scheme presently known or subsequently developed. Data collection module may also convert data from protocols used by data sources 207 to data formats acceptable to data processing module 202, as appropriate.

Data processing module 202 is any circuit, programming routine, application or other hardware/software module that is capable of processing data received from data collection module 206. In various embodiments, data processing module 202 is a software application executing on processor 102 (FIG. 1) to implement the process described below in conjunction with FIG. 3. Accordingly, data processing module suitably interprets received electrocardial or other data to identify episodes of myocardial ischemia and to classify the severity of any ischemia observed. By way of example and not of limitation, several systems and techniques for identifying and processing electrocardial data to identify ischemia are described in U.S. Pat. Nos. 6,324,421; 6,381,493 and 6,397,100 (which are incorporated herein by reference), although any other techniques could be used in alternate embodiments.

Ischemia can be detected, for example, when the patient's ST segment deviates from a baseline reading by more than a threshold amount, when the patient's cardiac conduction time exceeds a threshold value, or according to any other criteria. The baseline electrocardial data (e.g. baseline ST segment deviation or cardiac conduction time) may be a static value, or may be updated over time. In various embodiments, the baseline data represents a mean or median electrocardial value observed over any appropriate number of preceding samples. Threshold values may be any nominal values derived from a typical implanted cardioverter-defibrillator device (ICD) population of patients, or from any other source. Alternatively, the threshold values may be independently adjusted and set for a given patient as desired by the attending physician. For diagnosis purposes, the more recent values of ST segment deviation and/or conduction time, as well as other information, may be stored in a memory 204 along with the most recent arrhythmia to facilitate diagnosis of any association between the onset of ischemia and arrhythmia episodes.

In an exemplary embodiment, processing module 202 receives ECG waveform data 208 from data collection module 206 and interprets the data using conventional digital signal processing techniques to identify an ST segment of the waveform. If an episode of ischemia is identified, data about the episode (e.g. the amount of ST segment deviation, duration of the episode, time and date of the episode, and/or the like) may be stored in memory 204. Alternatively or additionally, processing module 202 identifies episodes of ischemia from cardiac conduction time data 216 or any other source(s) of data 207. Such information may also be stored within memory 204, which may correspond to hardware memory 104 shown in FIG. 1, or may be implemented with any other available digital storage device.

Data processing module 202 interprets collected data to gauge the severity of any ischemia observed. Elevation of the ST segment, for example, typically indicates a very severe form of ischemia and likely indicates myocardial infarction. Depression of the ST segment indicates ischemia of lesser severity. When ST segment depression is observed, data from other sources 207 (e.g. cardiac conduction time data 216) can be checked to verify that an incident of ischemia is indeed occurring. Further, data from a motion detector and/or accelerometer 212 can be incorporated to determine if the patient is active or at rest during the ischemic period to aid in determining whether the episode is stable or unstable. Stable ischemic episodes may also be checked against historical data stored in memory 204 to verify that the episode is consistent with prior episodes, and therefore does not warrant special attention. Alternate embodiments may identify and process episodes of ischemia using other data sources 207, as described more fully below.

After the severity of the particular episode is determined, processing module 202 triggers an appropriate response as warranted by the severity of the episode. Responses are activated by sending a digital message in the form of a signal, passed parameter or the like to response module 218 and/or reporting module 220.

Reporting module 220 is any circuit or routine capable of receiving an indication of ischemia and of producing appropriate feedback to the patient or to a physician. In various embodiments, suitable reports might include audible or visible alarms 228, wireless messages transmitted from a telemetry circuit 230 via an antenna 234, or other data that may be downloaded from a serial, parallel or other interface 232. Reports for particular ischemic episodes may vary with the severity of the episode. Minor episodes may result in no alarm at all, or a relatively non-obtrusive visual or audible alarm. More severe episodes might result in a more noticeable alarm, in addition to an automatic response as described below.

Telemetry circuitry 230 communicates an indication of the ischemic condition to an external device via antenna 234. The indication may be a wireless, radio frequency message that indicates an ischemic condition and, in some embodiments, the severity of the ischemic condition. The external device that receives the wireless message may be a programmer/output device that advises a physician or other attendant of the ischemic condition, e.g., via a display or a visible or audible alarm. Alternatively, the external device may be an interface to a telephone network such that IMD 100 is able to automatically notify emergency personnel if an extreme episode occurs.

Interface 232 is any serial, parallel or other interface to an external computing device. Interface 232 and/or telemetry circuit 230 may be used to provide information from IMD 100 to an external device. Information stored in memory 204 may be provided to an external digital computer or other device, for example, to aid in diagnosis or treatment of the patient.

Response module 218 is any circuit, software application or other component that interacts with any type of therapy-providing system 264, which may include any type of therapy deliver mechanisms such as a drug delivery system 222, neurostimulation 226 and/or electrocardial stimulation 224. In some embodiments, response module 218 may alternatively or additionally interact with an electrical stimulation therapy device integrated with IMD 100 to deliver pacing, post-extrasystolic potentiation, cardioversion and/or defibrillation therapy. Accordingly, the various responses to ischemic episodes that may be provided by IMD 100 vary from simple warnings to the patient to actual provision of therapy in various embodiments. Further, any therapy provided may be adjusted according to the severity of the particular episode. Drug dosage may be adjusted according to episode severity, for example, or pacing rates can be adjusted to respond to the severity of the particular episode.

The various components and processing modules of IMD 100 may be housed in a common housing such as that shown in FIG. 1. Alternatively, portions of IMD 100 may be housed separately. For example, portions of the therapy delivery system 264 could be integrated with IMD 100 or provided in a separate housing, particularly where the therapy delivery system includes drug delivery capabilities. In this case, response module 218 may interact with therapy delivery system 264 via an electrical cable or wireless link, or via interface 232.

Figure 3:
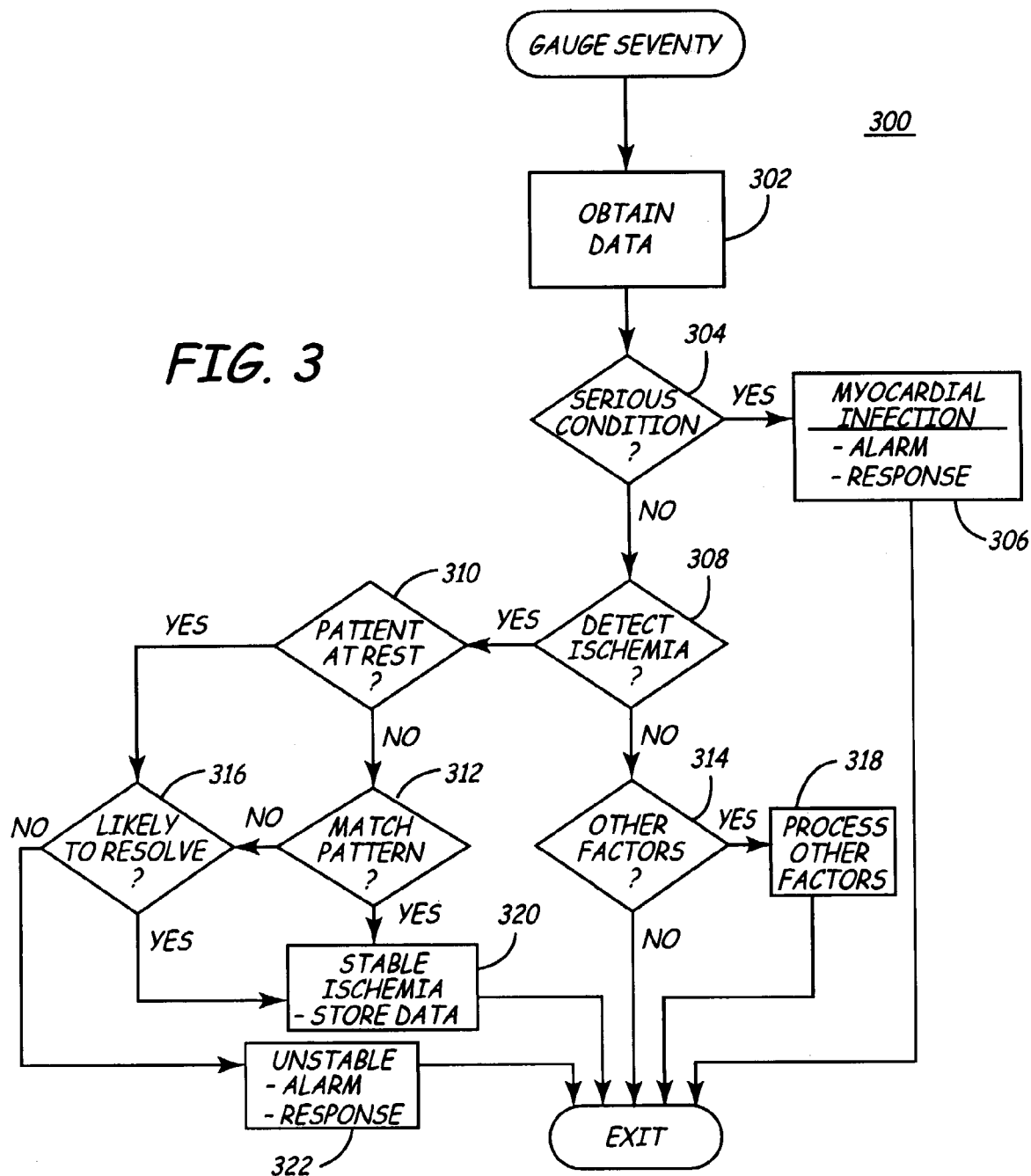
FIG. 3 is a flowchart of an exemplary process for detecting ischemia executed within an implantable medical device.

With reference now to FIG. 3, an exemplary process 300 for diagnosing and gauging the severity of ischemia suitably includes the broad steps of gathering data (step 302), processing the data to determine the severity of ischemia (e.g. steps 304, 308, 310, 312 and 316), and triggering an appropriate response (e.g. steps 306, 320, 322). In various embodiments, the various steps of process 300 may be implemented with computer-executable instructions that are stored in a digital memory 104 and that are appropriately executed by processor 102 (FIG. 1), or by any other processor associated with the IMD.

Process 300 suitably begins by obtaining data (step 302) at a data processing module 202 or other component in IMD 100 (FIG. 1). Data may include electrocardial information such as PQRST or ST waveform data, cardiac conduction times, accelerometer data or the like. Data may be collected according to any scheme, but in an exemplary embodiment data measurements are taken at regular time intervals with a sufficiently high frequency to identify any episodes of ischemia occurring with in the patient (e.g. on the order every few minutes or seconds). After data is obtained, it is formatted or otherwise processed as appropriate to put the data into a format that can be readily received and processed by data processing module 202 (FIG. 2) or another appropriate component of IMD 100. In a further embodiment, data from multiple sources is obtained and weighted with a scaling factor (i.e. a factor between 0–100%) to appropriately weigh the relative values of data obtained from the various sources. In such embodiments, ST segment deviation may be weighted higher than blood pH data, for example, during certain periods of observation. The relative weights assigned to the various factors may be programmable by a physician, and/or may vary according to time of day, level of patient exertion, amount of prior-diagnosed ischemia, or any other factors.

After data is obtained, it is suitably processed to identify and to gauge the severity of episodes of myocardial ischemia. Although an exemplary process 300 discussed herein emphasizes ischemia diagnosis through ST segment deviation for purposes of simplicity and illustration, other equivalent data factors such as cardiac conduction time, blood pH, blood pressure, cardiac accelerometer and the like may be used in addition to or in place of ST segment deviation in many alternate but equivalent embodiments.

In the embodiment shown in FIG. 3, serious conditions such as myocardial infarction (i.e. heart attack) are immediately identified (step 304). In one embodiment, ST segment data is analyzed to determine if the segment differs with respect to a baseline value by more than a threshold value, as described above. If ST segment elevation is identified in step 304, myocardial infarction is strongly indicated, and an appropriate response (step 306) is triggered. Alternatively, serious conditions may be identified through evaluation of other criteria such as cardiac conduction time, blood pressure, cardiac accelerometer data, or any other data obtained from sources 207 (FIG. 2). An appropriate response to myocardial infarction might include sounding an audible alarm, automatically contacting emergency personnel, and/or administering any available therapies such as drug therapy, electrostimulation, or neurostimulation as appropriate, and as described more fully below.

Even if no serious conditions exist, processing continues to identify episodes of ischemia (step 308). If ischemia is identified in step 308, then additional processing takes place to determine the severity of the ischemic condition observed. In an exemplary embodiment based upon ST segment monitoring, for example, ischemia may be indicated by ST segment depression. Alternatively, ischemia may be detected by considering cardiac conduction time, cardiac accelerometer readings, or any other factor(s). Generally speaking, ischemia can be presumed if the observed data value differs from a baseline by an amount that exceeds a threshold value, as described more fully above. In the case of ST segment deviation, deviations on the order of about 1 mm or more may be indicative of ischemia, although other threshold values could be used in alternate embodiments.

If ischemia is identified in step 308, additional factors (e.g. cardiac conduction time) may also be evaluated to verify that an ischemic condition exists, and that the differences observed in step 308 are not caused by other factors (e.g. physiological variants, etc.). Even if no ischemia is observed, processing may continue to consider additional factors such as cardiac conduction rate, blood pH, heart rate, and the like, if appropriate (steps 314, 318). In various embodiments, data may be stored within memory 104/204 even if ischemia is not identified, and such data may be used to compute baseline values, to aid a physician in diagnosis or treatment, or for any other purpose.

If ischemia is indeed identified (step 308), then processing continues to determine the severity of the ischemic episode. Severity may be determined using any number of factors, including whether the patient is active or at rest, whether the episode varies from prior episodes, the relative amount of affected tissue, the duration of the ischemic episode and the like. In the exemplary embodiment shown in FIG. 3, for example, accelerometer data may be interpreted to determine whether the patient is at rest (step 310), which in turn indicates whether the episode is stable or unstable. If the patient is determined to be in a period of exertion, IMD 100 may continue to monitor the situation to ensure that the depression ceases after the patient returns to rest. IMD 100 may also compare the most current data against stored data (step 312) to verify that the ischemic episode is consistent with prior episodes in terms of severity, frequency, duration and/or the like. If the episode is consistent with prior data and resolves spontaneously when the patient is at rest, then the episode is deemed to be stable ischemia (step 320) and an appropriate response can be generated. An alarm may be provided, for example, and data about the episode may be stored in memory 104/204 for subsequent analysis.

If the ischemic episode continues while the patient is at rest (step 310), however, or if the episode is inconsistent with prior episodes (step 312), then the episode is most likely an episode of unstable ischemia, which is typically a medical emergency. In some embodiments, further processing is conducted to determine if the episode is likely to resolve spontaneously (step 316). If so, the episode may be processed with less severity than otherwise required (step 320). If the episode is not likely to resolve spontaneously (step 316), however, the episode is deemed to be a more serious case of ischemia (step 322), and an appropriate response (e.g. alarm, notification of medical personnel, and/or application of therapy) is provided.

Figure 4:
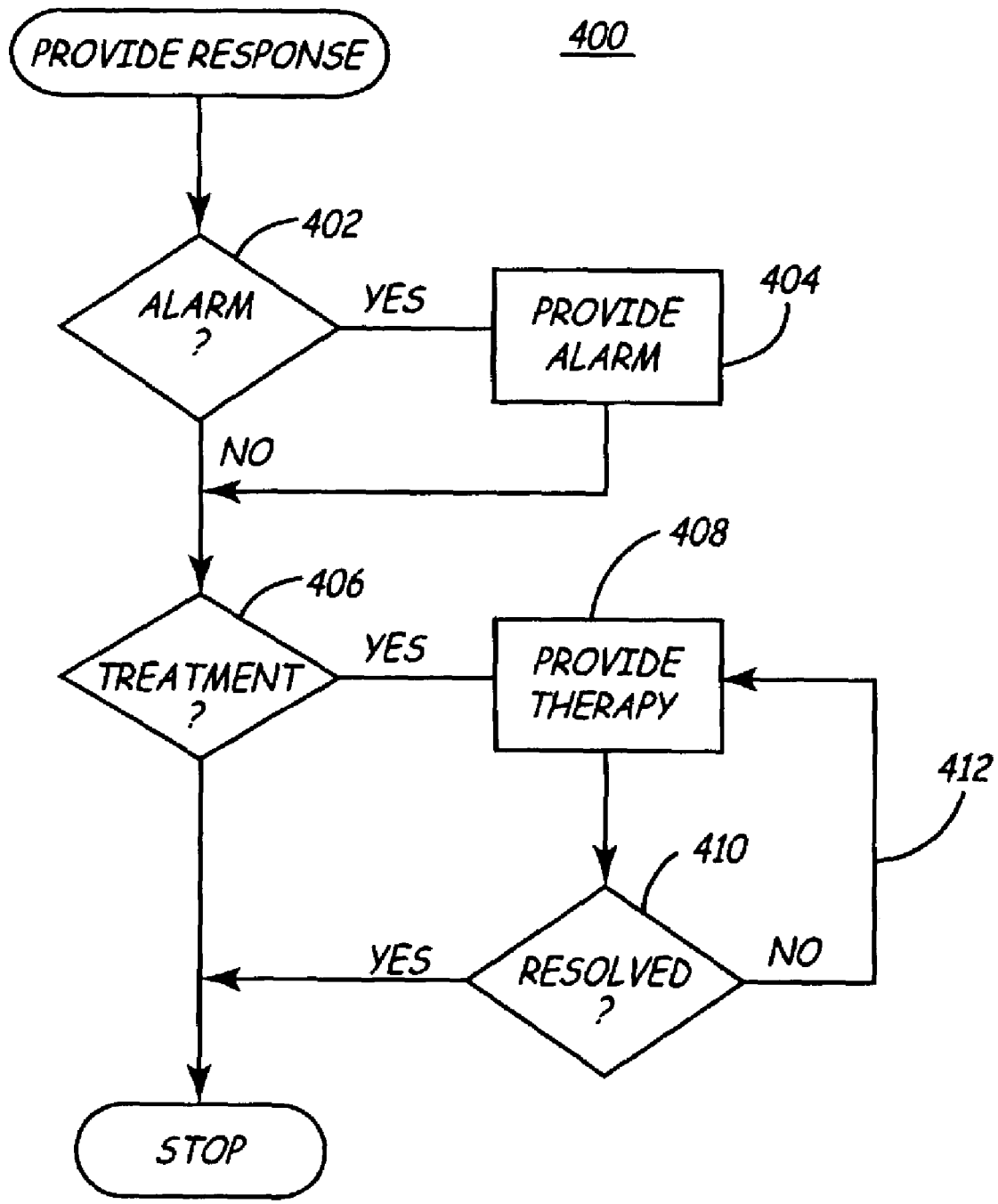
FIG. 4 is a flowchart of an exemplary process for providing a response to the patient during an ischemic episode.

With reference now to FIG. 4, an exemplary process 400 for providing a response to an observed ischemic episode suitably includes the steps of determining an appropriate response as a function of the severity of the episode (steps 402, 406), and then executing the response (steps 404, 408). If the episode warrants an alarm (step 402), an appropriate warning or alarm is provided to the patient (step 404) and/or to emergency personnel as described above. In embodiments that are capable of administering therapy during periods of ischemia, such treatment may be provided as appropriate (steps 406, 408). In further embodiments, therapies may be applied in a "closed loop" manner, whereby continuous monitoring of the patient's condition (step 410) is provided as feedback 412 to drive application of one or more therapies. Neurostimulation or other treatments, for example, may be applied in such magnitudes and durations as appropriate to bring the patient's cardiac condition back to normal. In such embodiments, pulse amplitude, pulse width, pulse frequency and/or other parameters can be monitored and/or titrated in a "closed loop" manner upon detection and grading of ischemia until the episode is relieved using conventional control techniques.

Accordingly, there is provided a method and apparatus for diagnosing and gauging the severity of myocardial ischemia. An implantable medical device is provided to the patient that is capable of diagnosing the patient's condition using, for example, electrocardial data. The device further processes the data to identify ischemic episodes of varying severity, and triggers a response that is appropriate for the particular episode identified. The device is further able to store data about the various episodes identified such that the patient can be made aware of ischemic conditions and so that the condition can be diagnosed and treated (e.g. with pharmaceuticals, lifestyle modifications, diet or the like) prior to the occurrence of a heart attack or other serious condition.

While exemplary embodiments have been presented in the foregoing detailed description of the invention, it should be appreciated that a vast number of variations exist. It should also be appreciated that these exemplary embodiments are only examples, and are not intended to limit the scope, applicability, or configuration of the invention in any way. Rather, the foregoing detailed description will provide a convenient road map for implementing an exemplary embodiment of the invention. Various changes may be made in the function and arrangement of elements described in an exemplary embodiment without departing from the scope of the invention as set forth in the appended claims and their legal equivalents.

What is claimed is:

1. A method executable by an implantable medical device (IMD) to detect ischemia in a patient's heart, the method comprising the steps of:

receiving data about at least one physiologic parameter related to the severity of an ischemic episode of a patient's heart via an IMD;

processing the data within the IMD to determine the severity of the ischemic episode, wherein said severity is deemed higher according to preselected criteria;

in the event that the severity of the ischemic episode exceeds a present value of a variable threshold, providing an alert signal from the IMD to the patient, wherein the alert signal is determined as a function of the severity of the ischemic episode; and modulating a palliative ischemia therapy based on the relative severity of the ischemic episode wherein the processing step comprises the steps of determining whether the ischemic episode can be classified as a stable ischemic episode or an unstable ischemic episode.

2. The method of claim 1 wherein the receiving step comprises receiving electrocardiogram (ECG) data.

3. The method of claim 2 wherein the processing step comprises interpreting an ST segment of the ECG data.

4. The method of claim 3 wherein the processing step further comprises interpreting accelerometer data.

5. The method of claim 1 further comprising:

gathering feedback data about the heart during a temporal interval subsequent to the time the data was received and while the alert signal is being provided, and adjusting the alert signal as a function of the feedback data.

6. The method of claim 1 wherein modulating the palliative ischemia therapy comprises providing a dose of an anti-ischemia medication dispensed from one of the IMD and an implantable drug-delivery device.

7. The method of claim 1 wherein the palliative therapy comprises providing an electrical signal in electrical communication with excitable tissue of the heart.

8. The method of claim 1 wherein the palliative therapy comprises a neurological stimualtion therpy.

9. The method of claim 1 further comprising the step of storing results data in a memory if the ischemic episode is classified as a stable ischemic episode.

10. A method of gauging the severity of ischemia in a patient's heart, the method comprising the steps of:

gathering electogram (EGM) data from a heart via an implantable medical device (IMD);

processing the EGM data to isolate an ST segment for the patient;

determining if the ST segment is one of elevated from a baseline and depressed from a baseline, and in the event that the ST segment is deemed elevated then classifying the event as an acutely severe episode of cardiac ischemia and in the event that the ST segment is deemed depressed then classifying the event as a relatively benign ischemic episode;

in the event that the ST segment is deemed depressed, then evaluating accelerometer data to determine is the ischemic episode can be further classified as one of a stable episode and an unstable episode; and issuing a response to the patient, wherein the response is determined as a function of whether the ischemic episode is one of: an acutely severe episode and an unstable episode.

11. The method of claim 10 further comprising the step of modulating an anti-ischemia therapy if the classification indicates an unstable ischemic episode.

12. The method of claim 10 further comprising the step of storing data in a memory if a stable ischemic episode is indicated.

13. An implantable medical device for gauging the severity of ischemia in a patient's heart, the device comprising:
   a data collection module configured to receive electrogram (EGM) data and accelerometer data about the condition of a patient's heart;
   a data processing module in communication with the data collection module and configured to process the EGM data and the accelerometer data to identify an episode of ischemia in the patient, wherein the data processing module is further configured to evaluate the EGM data and the accelerometer data to determine the relative severity of the episode; and
   a response module configured to provide a response to the patient as a function of the severity of the episode, said response including the delivering a modulated anti-ischemia therpy, wherein said therapy is modulated in relation to the relative severity of the episode
   wherein the processing module is further configured to identify the episode as a function of a depression in an ST segment portion of the EGM data and
   wherein the processing module is further configured to determine if the episode is stable or unstable as a function of the accelerometer data.

14. The device of claim 13 further comprising a response module configured to administer at least one additional anti-schemia therapy if the episode is classified as unstable, said additional anti-schemia therapy comprising one of: a drug therapy provided from an implantable drug pump and a neurological therapy delivered from an implantable pulse generator.

15. The device of claim 13 wherein the processing module is further operable to compare the episode to the historical data stored in the memory to verify that the episode is consistent with a pattern.

16. An implantable medical device (IMD) for gauging the severity of ischemia in a patient's heart, the device comprising:
   means for gathering electrogram (EGM) data from an implanted location disposed in electrical communication with a patient's heart;
   means for processing the EGM data to isolate an ST segment for the patient;
   means for determining if the ST segment is one or elevated from and depressed from a baseline level, wherein both an elevated and a depressed ST segment is deemed to indicate the detection of an ischemic episode;
   means for evaluating, if the ischemic episode is indicated, an accelerometer-based data set to determine if the ischemic episode is stable or unstable, wherein an accelerometer used to provide the accelerometer-based data set is adapted to mechanically couple to a portion of contractile tissue of the heart; and
   means for issuing a response to the patient, wherein the response is determined as a function of whether the ischemic episode is one of a stable episode and an unstable episode.

17. The device of claim 16 wherein the means for evaluating comprises a means for checking historical data regarding at least one prior ischemic episode for the patient to verify that the classified ischemic episode conforms to a historical pattern.

* * * * *

UNITED STATES PATENT AND TRADEMARK OFFICE
CERTIFICATE OF CORRECTION

PATENT NO. : 7,066,891 B2  
APPLICATION NO. : 10/325076  
DATED : June 27, 2006  
INVENTOR(S) : Robert W. Stadler et al.

Page 1 of 1

It is certified that error appears in the above-identified patent and that said Letters Patent is hereby corrected as shown below:

Col. 10, line 41, delete "therpy" and insert --therapy--

Col. 10, line 61, delete "is the" and insert --if the--

Col. 11, line 32, delete "anti-schemia" and insert --anti-ischemia--

Col. 11, line 33, delete "anti-schemia" and insert --anti-ischemia--

Signed and Sealed this

Twentieth Day of March, 2007

JON W. DUDAS  
*Director of the United States Patent and Trademark Office*